(12) United States Patent
Liu

(10) Patent No.: US 11,400,316 B2
(45) Date of Patent: Aug. 2, 2022

(54) MODERATOR FOR MODERATING NEUTRONS

(71) Applicant: NEUBORON MEDTECH LTD., Jiangsu (CN)

(72) Inventor: Yuan-Hao Liu, Jiangsu (CN)

(73) Assignee: NEUBORON MEDTECH LTD., Jiangsu (CN)

( * ) Notice: Subject to any disclaimer, the term of this patent is extended or adjusted under 35 U.S.C. 154(b) by 581 days.

(21) Appl. No.: 16/561,234

(22) Filed: Sep. 5, 2019

(65) Prior Publication Data
US 2021/0060360 A1 Mar. 4, 2021

Related U.S. Application Data

(63) Continuation of application No. PCT/CN2018/100384, filed on Aug. 14, 2018.

(30) Foreign Application Priority Data

Aug. 18, 2017 (CN) .......................... 201710710213.7

(51) Int. Cl.
A61N 5/10 (2006.01)
C04B 35/553 (2006.01)
(Continued)

(52) U.S. Cl.
CPC .......... A61N 5/1077 (2013.01); C04B 35/553 (2013.01); C04B 35/6455 (2013.01);
(Continued)

(58) Field of Classification Search
CPC ................ A61N 5/1077; C04B 35/553; C04B 35/6455; C04B 41/009; C04B 41/4842;
(Continued)

(56) References Cited

U.S. PATENT DOCUMENTS

2014/0299794 A1* 10/2014 Bennington .............. D01F 1/10
252/478
2015/0063524 A1* 3/2015 Yacout .................. G21C 21/02
427/6
(Continued)

FOREIGN PATENT DOCUMENTS

CN 101265099 A 9/2008
CN 101471157 A 7/2009
(Continued)

OTHER PUBLICATIONS

International Search Report of PCT/CN2018/100384, dated Nov. 5, 2018.

Primary Examiner — Nicole M Ippolito
(74) Attorney, Agent, or Firm — Locke Lord LLP; Tim Tingkang Xia, Esq.

(57) ABSTRACT

Disclosed is a moderator for moderating neutrons, including a substrate and a surface treatment layer or a dry inert gas layer or a vacuum layer coated on the surface of the substrate, wherein the substrate is prepared from a moderating material by a powder sintering device through a powder sintering process from powders or by compacting powders into a block, and the moderating material includes 40% to 100% by weight of aluminum fluoride; wherein the surface treatment layer is a hydrophobic material; and the surface treatment layer or the dry inert gas layer or the vacuum layer is used for isolating the substrate from the water in the environment in which the substrate is placed. The surface treated moderator can avoid the hygroscopic or deliquescence of the moderating material during use, improve the quality of the neutron source and prolong the service life.

20 Claims, 2 Drawing Sheets

(51) Int. Cl.
*C04B 35/64* (2006.01)
*C04B 41/00* (2006.01)
*C04B 41/48* (2006.01)
*C04B 41/49* (2006.01)
*C04B 41/83* (2006.01)
*C04B 41/84* (2006.01)
*G21K 1/00* (2006.01)
*H05H 3/06* (2006.01)
*C04B 35/645* (2006.01)

(52) U.S. Cl.
CPC ........ *C04B 41/009* (2013.01); *C04B 41/4842* (2013.01); *C04B 41/4961* (2013.01); *C04B 41/83* (2013.01); *C04B 41/84* (2013.01); *G21K 1/00* (2013.01); *H05H 3/06* (2013.01); *A61N 2005/109* (2013.01); *A61N 2005/1094* (2013.01); *A61N 2005/1095* (2013.01); *C04B 2235/3217* (2013.01); *C04B 2235/402* (2013.01); *C04B 2235/666* (2013.01)

(58) Field of Classification Search
CPC ..... C04B 41/4961; C04B 41/83; C04B 41/84; H05H 3/06
USPC ............... 250/505.1, 518.1, 492.1, 492.3
See application file for complete search history.

(56) References Cited

U.S. PATENT DOCUMENTS

| | | | | |
|---|---|---|---|---|
| 2015/0228363 | A1* | 8/2015 | Dewan | G21C 1/22 376/458 |
| 2016/0045841 | A1* | 2/2016 | Kaplan | C01B 32/05 429/49 |
| 2017/0216631 | A1 | 8/2017 | Pantell et al. | |

FOREIGN PATENT DOCUMENTS

| | | |
|---|---|---|
| CN | 102214488 A | 10/2011 |
| CN | 104332190 A | 2/2015 |
| CN | 104511096 A | 4/2015 |
| CN | 205004353 U | 1/2016 |
| CN | 106310540 A | 1/2017 |
| CN | 106938124 A | 7/2017 |
| EP | 2865658 A1 | 4/2015 |
| EP | 3032926 A1 | 6/2016 |
| EP | 3098209 A1 | 11/2016 |
| GB | 952090 A | 3/1964 |
| JP | 2006047115 A | 2/2006 |
| JP | 2014122375 A | 7/2014 |
| JP | 2016095158 A | 5/2016 |
| JP | WO2015111586 A1 | 3/2017 |
| WO | 2016177270 A1 | 11/2016 |
| WO | 2017118291 A1 | 7/2017 |

\* cited by examiner

MODERATOR FOR MODERATING NEUTRONS

RELATED APPLICATION INFORMATION

This application is a continuation of International Application No. PCT/CN2018/100384, filed on Aug. 14, 2018, which claims priority to Chinese Patent Application No. 201710710213.7, filed on Aug. 18, 2017, the disclosures of which are hereby incorporated by reference.

FIELD OF THE DISCLOSURE

The present disclosure relates to the field of medical devices, and in particular to a moderator for moderating neutrons.

BACKGROUND OF THE DISCLOSURE

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

BNCT takes advantage that the boron ($^{10}B$)-containing pharmaceuticals have high neutron capture cross section and produces $^4He$ and $^7Li$ heavy charged particles through $^{10}B(n,\alpha)^7Li$ neutron capture and nuclear fission reaction. As illustrated in FIGS. 1 and 2, a schematic drawing of BNCT and a nuclear reaction formula of $^{10}B$ $(n,\alpha)$ $^7Li$ neutron capture are shown, the two charged particles, with average energy at about 2.33 MeV, are of linear energy transfer (LET) and short-range characteristics. LET and range of the alpha particle are 150 keV/micrometer and 8 micrometers respectively while those of the heavy charged particle $^7Li$ are 175 keV/micrometer and 5 micrometers respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage. High-energy neutron rays irradiate normal cells, which can damage DNA and cause side effects such as skin inflammation and radiation anemia, and leukopenia. The epithermal neutron energy required for BNCT is low, while the average neutron energy produced by the neutron source is relatively high. Therefore, it is necessary to moderately filter the neutrons in different energy regions before irradiating the patient. At present, the commonly used moderating materials include aluminum, aluminum fluoride, aluminum oxide, magnesium fluoride, calcium fluoride, etc., but exposure of metal fluorides, such as aluminum fluoride and calcium fluoride, to air for a long period of time may cause physical and chemical changes, for instance, water absorption and even deliquescence, which may affect the performance of the material. Therefore, there is a need for a method that effectively avoids it.

SUMMARY

In order to provide a moisture-repellent moderator for moderating neutrons.

In a first aspect of the present disclosure provides a moderator including a substrate and a surface treatment layer or a dry inert gas layer or a vacuum layer coated on the surface of the substrate, wherein the substrate is prepared from a moderating material by a powder sintering device through a powder sintering process from powders or by compacting powders into a block, and the moderating material includes 40% to 100% by weight of aluminum fluoride; wherein the surface treatment layer is a hydrophobic material; and the surface treatment layer or the dry inert gas layer or the vacuum layer is used for isolating the substrate from the water in ambient air.

Implementations of this aspect may include one or more of the following features.

In another preferred embodiment, the surface treatment layer is a removable surface treatment layer.

In another preferred embodiment, the moderator further includes a first container, the inert gas layer is filled between the first container and the substrate, and the first container is for placing the substrate in the inert gas atmosphere.

In another preferred embodiment, the moderator further includes a second container, the vacuum layer is filled between the second container and the substrate, and the second container is for placing the substrate in the vacuum atmosphere.

In another preferred embodiment, the inert gas includes nitrogen, helium, neon, argon, krypton, xenon, or a combination thereof.

In another preferred embodiment, the moderating material includes 50 to 90% by weight of aluminum fluoride and optionally one or a mixture of two or more of lithium fluoride, aluminum, lead fluoride, aluminum oxide, calcium fluoride or magnesium fluoride.

In another preferred embodiment, the moderating material includes 90 to 99.9% by weight of aluminum fluoride and optionally 0.1 to 10% by weight of lithium fluoride.

In another preferred embodiment, the moderating material includes aluminum fluoride and lithium fluoride, and optionally one or a mixture of two or more of aluminum, lead fluoride, aluminum oxide, calcium fluoride or magnesium fluoride.

In another preferred embodiment, the powder sintering device is a hot press sintering device or a discharge plasma sintering device.

In another preferred embodiment, the powder sintering process is a hot press sintering process or a discharge plasma sintering process.

In another preferred embodiment, the surface treatment layer is a peelable surface treatment layer.

In another preferred embodiment, the surface treatment layer is selected from the group consisting of a hydrophobic organic polymer, a hydrophobic inorganic polymer, or a combination thereof.

In another preferred embodiment, the hydrophobic organic polymer is selected from the group consisting of an organic fluoropolymer, a silicone polymer, a C2-20 substituted or unsubstituted olefinic polymer, a C2-20 substituted or unsubstituted alkynylic polymer, or a combination thereof.

In another preferred embodiment, the hydrophobic material is a hydrophobic material having a contact angle θ of 110 to 180° with water, preferably having a contact angle θ of 120 to 180°, and more preferably a contact angle θ of 130 to 180°.

In another preferred embodiment, the surface treatment layer is selected from the group consisting of an elemental metal, an alloy, a metal oxide, a metal fluoride, a metal nitride, a metal carbon oxynitride, silicon oxide, silicon nitride, or a combination thereof; wherein, any of the "metals" is a non-deliquescent metal, that is, does not absorb or does not substantially absorb moisture in the air, and does not change or does not substantially change in chemical properties in an aqueous environment.

In another preferred embodiment, the metal fluoride is selected from the group consisting of magnesium fluoride, calcium fluoride, barium fluoride, lead fluoride, or a combination thereof.

In another preferred embodiment, the surface treatment layer is coated on the surface of the substrate by a method selected from the group consisting of covering, wrapping, pasting, electroplating, evaporation plating, electroless plating, spray plating, spray coating, dipping, vacuum evaporation, sputtering, deposition, or a combination thereof.

In another preferred embodiment, the surface treatment layer is a single layer or a multi-layer structure, and the multi-layer structure includes two-layer, three-layer, four-layer and five-layer structure; and the layers in the multi-layer structure are the same material or different materials.

In another preferred embodiment, the surface treatment layer has a thickness of 0.01 to 100 μm.

In another preferred embodiment, the surface treatment layer has a thickness of 0.05 to 50 μm.

In another preferred embodiment, the surface treatment layer has a thickness of 0.1 to 10 μm.

In another preferred embodiment, the moderator is provided in a shape of two tapered sections that are adjacent to each other in opposite directions.

In another preferred embodiment, the moderator includes a first diameter, a second diameter, and a third diameter, the length of the first diameter is 1 cm to 20 cm, the length of the second diameter is 30 cm to 100 cm, the length of the third diameter is 1 cm to 50 cm, and the material of the moderator has a density of 80% to 100% of the theoretical density.

In a second aspect of the present disclosure, a beam shaping assembly is provided, including the moderator according to the first aspect of the present disclosure, a beam inlet, a target, a reflector adjacent to the target and surrounding the moderator, a thermal neutron absorber adjacent to the moderator, and a radiation shield disposed within the beam shaping assembly and a beam exit.

In another preferred embodiment, the moderator for moderating neutrons, comprising: a substrate prepared from a moderating material by a powder sintering device through a powder sintering process from powders or by compacting powders into a block, wherein the moderating material comprises 40% to 100% by weight of aluminum fluoride, and a surface treatment layer or a dry inert gas layer or a vacuum layer coated on the surface of the substrate, wherein the surface treatment layer is a hydrophobic material; and the surface treatment layer or the dry inert gas layer or the vacuum layer is provided for isolating the substrate from the water in ambient air, wherein the moderator is provided for a beam shaping assembly, the beam shaping assembly including: a beam inlet, a target reacted with a proton beam from the beam inlet to produce neutrons, a reflector adjacent to the target and surrounding the moderator, wherein the reflector leads deflected neutrons back to enhance epithermal neutron beam intensity, a thermal neutron absorber adjacent to the moderator, wherein the thermal neutron absorber is used for absorbing thermal neutrons so as to avoid overdosing in superficial normal tissue during therapy, a radiation shield disposed within the beam shaping assembly, wherein the radiation shield is provided for shielding leaking neutrons and photons so as to reduce dose of the normal tissue not exposed to irradiation, and a beam exit.

In another preferred embodiment, the beam shaping assembly further includes a third container, wherein the inert gas layer is located between the third container and the substrate, and the third container is for placing the substrate of the moderator in an inert gas atmosphere as described in the first aspect.

In another preferred embodiment, the beam shaping assembly further includes a fourth container, wherein the vacuum layer is filled between the fourth container and the substrate, and the fourth container is for placing the substrate of the moderator in the vacuum atmosphere.

In another preferred embodiment, the beam shaping assembly further includes a fifth container, wherein the fifth container is for placing the moderator, beam inlet, target, reflector, thermal neutron absorber, radiation shield, and beam exit of the shaping assembly in the inert gas atmosphere as described in the first aspect.

In another preferred embodiment, the beam shaping assembly is used for an accelerator boron neutron capture therapy, and the accelerator boron neutron capture therapy accelerates the proton beam by an accelerator, the target is made of metal, the proton beam is accelerated to an energy sufficient to overcome the coulomb repulsion of the target nucleus and undergo a nuclear reaction with the target to produce neutrons, the beam shaping assembly can slow the neutrons to the epithermal neutron energy region and reduce the contents of thermal neutron and fast neutron, the epithermal energy region is between 0.5 eV and 40 keV, the thermal neutron energy region is less than 0.5 eV, and the fast neutron energy region is greater than 40 keV, the reflector is made of a material having a strong neutron reflection ability, and the thermal neutron absorber is made of a material having a large cross section with thermal neutrons.

In a third aspect of the present disclosure, a moderator for moderating neutrons is provided, including: a substrate prepared from a moderating material by a powder sintering device through a powder sintering process from powders or by compacting powders into a block, wherein the moderating material comprises 40% to 100% by weight of aluminum fluoride, and a surface treatment layer or a dry inert gas layer or a vacuum layer coated on the surface of the substrate, wherein the surface treatment layer is a hydrophobic material; and the surface treatment layer or the dry inert gas layer or the vacuum layer is provided for isolating the substrate from the water in ambient air, wherein the moderator is provided in a shape of two tapered sections that are adjacent to each other in opposite directions and for a beam shaping assembly, the beam shaping assembly including: a beam inlet, a target reacted with a proton beam from the beam inlet to produce neutrons, a reflector adjacent to the target and surrounding the moderator, wherein the reflector leads deflected neutrons back to enhance epithermal neutron beam intensity, a thermal neutron absorber adjacent to the moderator, wherein the thermal neutron absorber is used for absorbing thermal neutrons so as to avoid overdosing in superficial normal tissue during therapy, a radiation shield disposed within the beam shaping assembly, wherein the radiation shield is provided for shielding leaking neutrons and photons so as to reduce dose of the normal tissue not exposed to irradiation, and a beam exit.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

In order to illustrate the technical solutions of the embodiments of the present disclosure more clearly, the drawings to be used in the embodiments of the present disclosure will be briefly described below. Obviously, the drawings in the following description are only some embodiments of the present disclosure, and those skilled in the art can obtain other drawings according to the drawings without any creative work.

Figure 1:
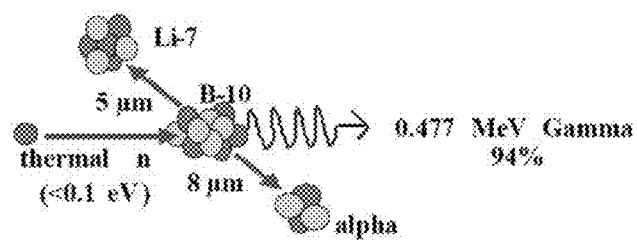
FIG. 1 is a schematic diagram of a boron neutron capture reaction.
Figure 2:
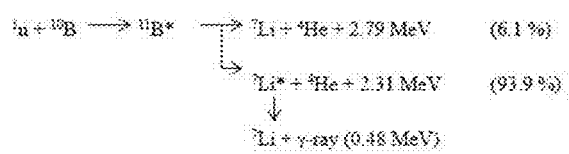
FIG. 2 is a $^{10}B(n,\alpha)$ $^{7}Li$ neutron capture nuclear reaction equation.

Wherein, 1 is a beam shaping assembly, 2 is a beam inlet, 3 is a target, 4 is a moderator adjacent to the target, 5 is a reflector surrounding the moderator, 6 is a thermal neutron absorber adjacent to the moderator, 7 is a beam outlet, 401 is a surface treatment layer, and 402 is a substrate.

DETAILED DESCRIPTION

Through extensive and intensive research, the inventors have invented a moderator for moderating neutrons, includes a moderating material aluminum fluoride which is hygroscopic and deliquescent. By coating the surface treatment layer on the surface of the substrate of the moderator, the moderating material can be prevented from gradual moisture absorption and deliquescence during use, and the quality of the neutron source is improved and the service life is prolonged.

The surface treatment layer of the present disclosure includes a hydrophobic organic polymer, a hydrophobic inorganic polymer, an elemental metal, an alloy, a metal oxide, a metal fluoride, a metal nitride, a metal carbon oxynitride, silicon oxide, silicon nitride, or a combination thereof. The hydrophobic organic polymer is selected from the group consisting of an organic fluoropolymer, a silicone polymer, a C2-20 substituted or unsubstituted olefinic polymer, a C2-20 substituted or unsubstituted alkynylic polymer, or a combination thereof. Wherein, the C2-20 substituted or unsubstituted olefinic polymer refers to a substituted or unsubstituted linear or branched olefin polymer having 2 to 20 carbon atoms, and by "substituted" is meant that the olefin polymer is substituted with one, two, three, four substituents selected from the group consisting of methyl, ethyl, propyl, fluorine, chlorine, bromine, sulfur, oxygen, phenyl, benzyl. For example, polytetrafluoroethylene, polystyrene, and polypropylene. Wherein, the C2-20 substituted or unsubstituted alkynylic polymer refers to a substituted or unsubstituted linear or branched alkyne polymer having 2 to 20 carbon atoms, and by "substituted" is meant that the alkynylic polymer is substituted with one, two, three, four substituents selected from the group consisting of methyl, ethyl, propyl, fluorine, chlorine, bromine, sulfur, oxygen, phenyl, benzyl. For example, polytetrafluoroacetylene, polyphenylacetylene, and polypropyne. The hydrophobic material is a hydrophobic material having a contact angle θ of 110 to 180° with water, preferably having a contact angle θ of 120 to 180°, and more preferably a contact angle θ of 130 to 180°.

The number of layers of the surface treatment layer is not particularly limited, and is preferably a single layer, two layers, three layers, four layers, or five layers; the layers may be the same material or different materials. The thickness of the surface treatment layer is not particularly limited, and is preferably 0.01 to 100 μm, more preferably 0.1 to 10 μm.

The surface treatment layer may be a peelable surface treatment layer or a non-peelable surface treatment layer. The coating method of the surface treatment layer is not particularly limited, and is preferably coated on the surface of the substrate by a method selected from the group consisting of covering, wrapping, pasting, electroplating, evaporation plating, electroless plating, spray plating, spray coating, dipping, vacuum evaporation, sputtering, deposition, or any combination thereof. For example, the hydrophobic material is tightly covered on the surface of the substrate to isolate water in the environment, or the surface treatment layer is coated on the substrate by any of the film forming methods described.

The dry inert gas layer or vacuum layer coated on the surface of the substrate of the present disclosure means that the substrate is placed in a dry inert gas atmosphere or a vacuum atmosphere, and the substrate is isolated from water, especially water in the air by the inert gas layer or the vacuum layer. Preferably, the moderator further includes a first container, the inert gas layer is located between the first container and the substrate, and the first container is for placing the substrate in an inert gas atmosphere. Wherein, the inert gas includes nitrogen, helium, neon, argon, krypton, xenon, or a combination thereof. Preferably, the moderator further includes a second container, the vacuum layer is located between the second container and the substrate, and the second container is for placing the substrate in a vacuum atmosphere. Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components include, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^{7}Li$ (p, n) $^{7}Be$ and $^{9}Be$ (p, n) $^{9}B$ and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

The disclosure is further illustrated by the following specific examples. It is to be understood that the following description is only the most preferred embodiment of the disclosure and should not be construed as limiting the scope of the disclosure. The experimental methods in the following examples which do not specify the specific conditions, generally according to the conventional conditions, or according to the conditions recommended by the manufacturer, those skilled in the art can make non-essential changes to the technical solutions of the present disclosure, and such modifications should be considered as being included in the scope of protection of the present disclosure. Unless otherwise stated, percentages and parts are by weight and parts by weight.

Figure 3:
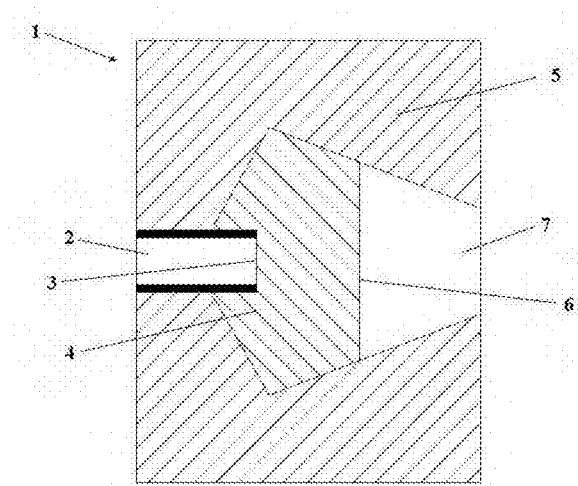
FIG. 3 is a schematic plan view of a moderator for moderating neutrons in an embodiment of the present disclosure, wherein the moderator is disposed as two tapered sections.

In order to improve flux and quality of neutron sources, the embodiments of the present disclosure provides improvement of a beam shaping assembly for neutron capture therapy, preferably, improvement of a beam shaping assembly for AB-BNCT. As shown in FIG. 3, the beam shaping assembly 1 for neutron capture therapy in the first embodiment of the present disclosure includes a beam inlet 2, a target 3, a moderator 4 adjacent to the target, a reflector 5 surrounding the moderator, a thermal neutron absorber 6 adjacent to the moderator, and a beam outlet 7. The target has nuclear reaction with an incident proton beam from the beam inlet to produce neutrons; the neutrons form a neutron beam, the neutron beam defines a main axis X, and the neutrons are moderated by the moderator to epithermal neutron energies, and the reflector leads the neutrons deviated from the main axis X back to enhance epithermal neutron beam intensity; a gap channel is placed between the moderator and the reflector so as to increase the epithermal neutron flux; the thermal neutron absorber is used for absorbing thermal neutrons so as to avoid overdosing in superficial normal tissue during therapy; the radiation shield 16 is used for shielding the leaking neutrons and photons so as to reduce dose of a normal tissue not exposed to irradiation.

AB-BNCT accelerates a proton beam using an accelerator. Preferably, the target is made of a metal material, and the proton beam is accelerated enough to overcome coulomb repulsion energy of a target atomic nucleus and has $^7$Li (p, n) $^7$Be reaction with the target to produce neutrons. The beam shaping assembly 10 moderates the neutrons into epithermal neutron energies and reduces the quantity of thermal neutrons and fast neutrons; the moderator is made of a material having a cross section for principally acting with fast neutrons but hardly acting with epithermal neutrons. Preferably, the moderator is made of at least one of $D_2O$, $AlF_3$, Fluental™, $CaF_2$, $Li_2CO_3$, $MgF_2$ and $Al_2O_3$. The reflector is made of a material having high neutron reflection ability, and is made of at least one of Pb or Ni preferably. The thermal neutron absorber is made of a material having a cross section for acting with thermal neutrons and is made of $^6$Li preferably. An air passage 19 is placed between the thermal neutron absorber and the beam outlet. The radiation shield includes a photon shield and a neutron shield, and includes a photon shield made of lead (Pb) and a neutron shield made of polyethylene (PE) preferably.

Figure 4:
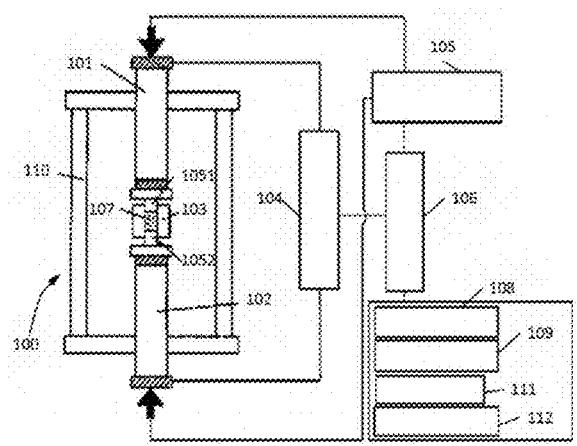
FIG. 4 is a schematic view of a preparation device of a moderator material in an embodiment of the present disclosure, wherein the preparation device is a discharge plasma sintering device.

Refer to FIG. 4, it discloses a schematic view of a spark plasma sintering device. The spark plasma sintering device 100 includes a first electrode 101, a second electrode 102, a conductive mold 103 arranged between the first electrode 101 and the second electrode 102, a pulse current generator 104 for providing pulse current for the mold 103, a pressing assembly 105 with pressing members 1051, 1052 for pressing the powders or powder compacts, and a controller 106 for controlling the pulse current generator 104 and the pressing assembly 105, at least one of the first electrode 101 and the second electrode 102 can be moved, and at least one of the pressing members 1051, 1052 can be moved; as a preference, the first electrode 101 and the pressing part 1051 are fixed, the second electrode 102 and the pressing part 1052 can be moved, and thereby powders or powder compacts 107 loaded in the mold 103 can be pressed. As a preference, the conductive mold 103 is of lead or graphite. The spark plasma sintering device 100 further includes a position measurement system 108 for measuring the position of the pressing assembly 105, an atmosphere control system 109 for controlling atmosphere in the mold 103, a water cooling system 111 for controlling a water-cooling vacuum chamber 110 to carry out cooling, and a temperature measurement system 112 for measuring temperature in the spark plasma sintering device 100. Pulse current is applied to the mold 103 and the powders or powder compacts 107; besides providing discharge impact pressure and Joule heat for sintering, a sintering promotion effect caused by a spark discharge phenomenon (the instantaneous generation of high-temperature plasma) generated in powder at the initial stage of pulse discharge is further utilized to implement rapid sintering through an instantaneous high temperature field, so that the powders or powder compacts 107 are turned into blocks from the powder state, and the so-called blocks are integrally formed without needing, for example, putting together monocrystals by steps, such as grinding or polishing, to match the dimensions of the moderator, like the crystal growing method.

The spark plasma sintering device 100 utilizes direct-current pulse current to be directly electrified for sintering and pressing, and controls the rate of temperature rise and sintering temperature by regulating the magnitude of the direct-current pulse current through the controller 106. The whole sintering process can be carried out under a vacuum environment, or can be carried out in protective atmosphere, such as oxygen or hydrogen.

Under oxygen atmosphere, because oxygen is adsorbed by the surface of the sinter or chemical reaction occurs, a cation vacancy type non-stoichiometric compound is formed on the surface of the crystal, cation vacancies are increased, meanwhile, oxygen in closed apertures can directly get into the crystal lattice, and is diffused along the surface like oxygen ion vacancies, and diffusion and sintering are accelerated. When sintering is controlled by cation diffusion, oxidizing atmosphere or oxygen partial pressure is high and favorable for the formation of the cation vacancies, promoting sintering; and when sintering is controlled by anion diffusion, reducing atmosphere or low oxygen partial pressure will lead to the generation of oxygen ion vacancies and promote sintering.

When a sample is sintered under hydrogen atmosphere, as the radius of the hydrogen atom is very small, hydrogen is easy to diffuse and beneficial to elimination of closed apertures, and when a type of material, such as alumina, is sintered under the hydrogen atmosphere, a sinter sample which approximates theoretical density can be obtained.

Sintering temperature is one of key parameters in the process of plasma rapid sintering. The determination of a sintering temperature must take the phase transformation of the sinter sample under high temperature, the growth rate of a crystalline grain, the requirement on the quality of the sample and the requirement on the density of the sample into consideration. In general, as sintering temperature rises, the overall compactness of a test sample tends to increase, this indicates that sintering temperature has remarkable influence on the compactness degree of the sample, and the higher sintering temperature is, the higher the speed of substance transmission is in the process of sintering and the easier the sample is to compact.

However, the higher temperature is, the higher the growth rate of a crystalline grain is and the poorer its mechanical properties are. When temperature is too low, the compactness of the sample is very low, and quality cannot meet a requirement. Due to the contradiction between temperature and crystalline grain size, an appropriate parameter is required in respect of temperature choice.

Normally, prolonging temperature keeping time under sintering temperature will promote the completion of sintering to different degrees and perfect the microstructure of the sample, which is more obvious for sintering for a viscose flow mechanism while having less influence on sintering for bulk diffusion and surface diffusion mechanism. In the process of sintering, normally, when temperature is kept for only one minute, the density of the sample reaches not less than 96.5 percent of theoretical density; as temperature keeping time extends, the compactness of the sample increases, but the variation range is not broad, and this indicates that although the temperature keeping time has certain influence on the compactness of the sample, the effect of action is not remarkable. However, if the temperature keeping time under the sintering temperature is prolonged unreasonably, the crystalline grain will rapidly grow within the time, intensifying secondary recrystallization, which is adverse to a requirement on the properties of the sample, and if the time is too short, it will cause a decrease in the compactness of the sample, so it is necessary to choose an appropriate temperature keeping time.

With an increase in the rate of temperature rise, the sample reaches a required temperature within a short time, the growth time of the crystalline grain will be greatly shortened, and this not only helps to inhibit the crystalline grain from growing up, so that a fine-grained ceramic with uniform size can be obtained, but also can save time and energy and increase the utilization rate of the sintering device. However, due to the limitation of the device, an over high rate of temperature rise will cause a destructive effect on the device. For this reason, the rate of temperature rise should be increased as much as possible within an allowable range. Nevertheless, it is reflected in measured experimental data that different from sintering temperature and temperature keeping time, the influence of the rate of temperature rise on sample compactness shows an opposite result, that is, as the rate of temperature rise increases, sample compactness shows a tendency of coarsening and gradually decreasing. Some scholars have suggested that this is because the increase of the rate of temperature rise near sintering temperature is equivalent to the shortening of temperature keeping time, so sample compactness will decrease to a certain degree. In an actual high-temperature sintering process, the temperature rise process is normally divided into three stages, i.e. a stage from room temperature to about 600° C., a stage from 600° C. to about 900° C. and a stage from 900° C. to a sintering temperature: the first stage is a preparation stage, and the rate of temperature rise is relatively slow; the second stage is a controllable rapid temperature rise stage, and the rate of temperature rise is normally controlled at 100 to 500(° C./min); the third stage is a buffering stage of temperature rise, temperature is slowly increased to the sintering temperature at this stage, the temperature keeping time is normally one to seven minutes, a sinter is cooled along with the furnace after temperature keeping, and the cooling rate can reach 300° C./min.

After sufficient discharge treatment, powders are immediately pressed to be shaped and sintered. The sintered material is severely plastically deformed under the combined action of resistance Joule heat and pressure, applying forming pressure can help to enhance the contact between the powder grains, enlarge sintering area, exhaust residual gas in the sintered powder and increase the strength, density and surface smoothness of a product. The magnitude of forming pressure is normally determined according to the compactness of the sintered powder and requirements on the properties of the sintered material, such as density and strength, and is normally within a range from 15 MPa to 30 MPa, and sometimes, may be as high as 50 MPa or even higher. Usually, the higher forming pressure is, the density of the sintered material is. The duration of pressure application will also greatly affect the density of the sintered material, and depending on varieties of sintered materials, powder grain sizes and geometrical dimensions of the sintered materials, appropriate pressure application time may be different, and needs to be determined by experiments. An experiment proves that the duration of pressure application is equal to or slightly greater than discharge time, and this is a necessary condition to obtain a sintered material with the highest density. It is easy to understand from a sintering and solid-phase reaction mechanism that the higher pressure is, the more tightly grains in a sample heap, mutual contact points and contact areas are enlarged, and sintering is accelerated. Thus, the sample can obtain better compactness, moreover, the crystalline grain can be effectively inhibited from growing up, and sintering temperature can be decreased. Therefore, chosen pressure is normally 30 Mpa to 50 MPa. Nevertheless, a research indicates that during sintering, when external pressure is 30 MPa and 50 MPa, the difference between the compactness of the sample is not great, and this suggests that the phenomenon that compactness increases along with pressure is only obvious within a certain range.

Compared with conventional sintering techniques, spark plasma sintering has the following advantages: sintering speed is high; material microstructures are improved, and the properties of materials are increased.

As known well by those skilled in the art, the mold can be produced by using other conductive materials, the spark plasma sintering device can also be so arranged that both electrodes are fixed, while only at least one pressing member can move.

The main process flow of spark plasma sintering is divided into four stages in total. First stage: initial pressure is applied to a powder sample to make the powder grains be in sufficient contact with one another, so that uniform and sufficient spark plasma can be generated in the powder sample later; Second stage: pulse current is applied, the contact points of the powder grains generate spark plasma under the effect of the pulse current, and the grain surfaces generate a slight heat releasing phenomenon due to activation; Third stage: a pulse power supply is switched off, resistance heating is carried out on the sample until the sample reaches a predetermined sintering temperature and the contraction of the sample is complete; Fourth stage: pressure is released. By reasonably controlling main technological parameters, such as initial pressure, sintering time, forming time, pressure application duration, sintering temperature and the rate of temperature rise, a material with good comprehensive properties can be obtained.

Due to a bridging effect between the powder grains, they cannot be in sufficient contact normally, so, in order to generate uniform and sufficient-discharge plasma in the sample during spark sintering and activate the grain surfaces to the max to accelerate the sintering compaction process, appropriate initial pressure needs to be applied to the sintered powders, so that the powder grains can be in sufficient contact. The magnitude of initial pressure may be different, depending on varieties of sintered powders and sizes and properties of sinters. If initial pressure is too low, the discharge phenomenon will be only limited to part of the powders, leading to the partial melting of the powders; if initial pressure is too high, discharge will be inhibited, and the sintering diffusion process will then be retarded. According to existing literature, in order to make discharge proceed continuously and sufficiently, the initial pressure should not exceed 10 MPa normally.

When a powder test sample with good spark sintering conductivity is used, because resistance heating is carried out simultaneously from the outside and inside of the sample, the sintering time is extremely short or even instantaneous, but the length of the sintering time should be different according to qualities, varieties and properties of powders, and is normally several seconds to several minutes; and when a large, difficult-to-melt metal powder material is sintered, the sintering time is even up to tens of minutes. Sintering time has great influence on the density of the product, and in order to make the compaction process proceed sufficiently, a certain sintering time needs to be guaranteed.

It is generally believed that rapid temperature rise in the process of spark plasma sintering is beneficial to the sintering of powders because it inhibits the non-compaction mechanism of the material and activates the compaction mechanism of the material, so increasing the rate of temperature rise can make the compaction degree of the sample increased.

As a preference, the spark plasma sintering process includes the following steps: filling the mold 103 with an appropriate amount of powders or powder compacts 107; moving the pressing assembly 105 to press the powders or powder compacts 107 in the mold 103; switching on, by utilizing the controller 106, the pulse current generator 104 to electrify the mold 103, so that plasma is generated and the surfaces of the powder grains are activated and heat; and sintering the powders or powder compacts 107 into blocks. The spark plasma sintering process further includes the following steps: the controller 106 controls the position measurement system 108 to ensure the normal operation of the position measurement system 108, the controller 106 controls the atmosphere control system 109 to ensure that atmosphere in the mold 103 is under the condition of normal operation, the controller 106 controls the water cooling system 111 to ensure that it is under the condition of normal operation, and the controller 106 controls the temperature measurement system 112 to ensure that temperature in the spark plasma sintering device 100 is under the condition of normal operation. The so-called normal operation means that the spark plasma sintering device does not generate visual, tactile or auditory warning signals perceivable by the human being, such as the shining of a warning indicator light, the sounding of the warning indicator light, warning indicator vibration and the like.

Hot-press sintering is a sintering method in which dry powder is loaded into the mold, and is then pressed in a single-axis direction while being heated, so that forming and sintering are complete at the same time. The hot-press sintering technique is rich in production processes, and there are no unified specifications and standard for classification at present. According to current situation, the production processes can be divided into vacuum hot pressing, hot pressing under atmosphere, vibratory hot pressing, balanced hot pressing, hot isostatic pressing, reaction hot pressing and ultrahigh-pressure sintering. Since heating and pressing are carried out simultaneously in hot-press sintering, the powder is in a thermoplastic state, which is favorable for the proceeding of the contact diffusion and flowing mass transfer process of the grains, and therefore forming pressure is only one tenth of that in cold pressing; furthermore, sintering temperature can be decreased, sintering time can be shortened, and thereby the crystalline grain is inhibited from growing up, obtaining a product with a fine crystalline grain, high compactness and good mechanical and electrical properties.

Figure 5:
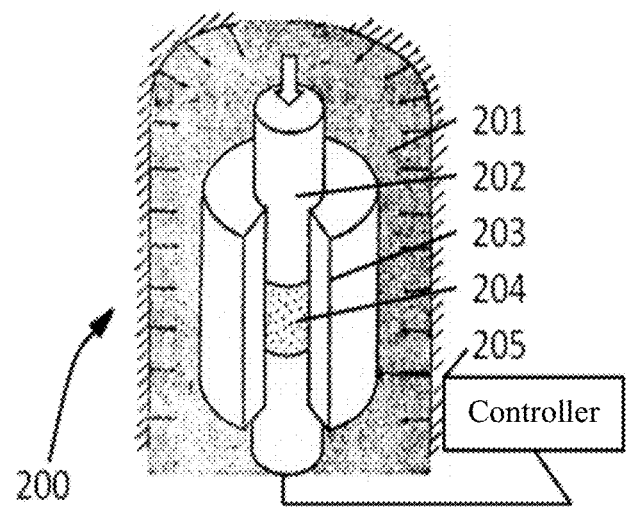
FIG. 5 is a schematic view of a preparation device of a moderator material in an embodiment of the present disclosure, wherein the preparation device is a hot press sintering device.

In order to adopting the hot-press sintering process to prepare a moderator material, refer to FIG. 5, a hot-press sintering device 200 mainly includes a heating furnace 201, a pressing assembly 202 arranged in the heating furnace 201, a mold 203, powders or powder compacts 204 loaded in the mold 203, and a controller 205. The heating furnace 201 normally adopts electricity as a heat source, and a heating element is made of a SiC, MoSi or nichrome wire, a platinum wire, a molybdenum wire, etc. The pressing assembly 202 is required to be steady and slow in speed, constant in pressure keeping and flexible in pressure regulation, and normally, there are a lever type and a hydraulic type. According to the requirement of material properties, pressurized atmosphere can be air, as well as reducing atmosphere or inert atmosphere. The mold 203 is required to be high in strength, high temperature resistant, oxidation resistant and not sticking with a hot-pressed material, the thermal expansion coefficient of the mold 203 should be consistent with or approximate that of the hot-pressed material, and as a preference, a graphite mold is adopted in the present embodiment. The controller 205 ensures that the hot-press sintering device 200 is under the condition of normal operation. The so-called normal operation means that the spark plasma sintering device does not generate visual, tactile or auditory warning signals perceivable by the human being, such as the shining of a warning indicator light, the sounding of the warning indicator light, warning indicator vibration and the like.

Taking adopting the hot-press sintering process to prepare a target moderator from $MgF_2$ as an example, the production process flow generally includes the following steps: preparation of $MgF_2$ material—grinding and screening of material—transferring into mold—high-temperature sintering—high-temperature hot-press sintering—cooling and discharge—hot isostatic pressure—high-temperature sintering—cooling and discharge—grinding, polishing and bonding—finished product.

As a preference, the preceding powder treatment step and the succeeding treatment step for sintering completion are omitted here. The hot-press sintering process includes the following steps: filling the mold 203 with an appropriate amount of powders or powder compacts 204; switching on the hot-press furnace 201 to preset pressure and temperature parameters; moving the pressing assembly 202 to press the powders or powder compacts 204 in the mold 203; controlling, by the controller 205, the hot-press sintering device 200 to be under the condition of normal operation; and switching on power to sinter the powders or powder compacts 204 into blocks.

It needs to be further explained that the step "moving the pressing assembly 202 to press the powders or powder compacts 204 in the mold 203" in the hot-press sintering process can be prepressing or carried out as the power is switched on, that is, the step "moving the pressing assembly 202 to press the powders or powder compacts 204 in the mold 203" and the step "switching on power to sinter the powders or powder compacts 204 into blocks" are integrated.

Figure 6:
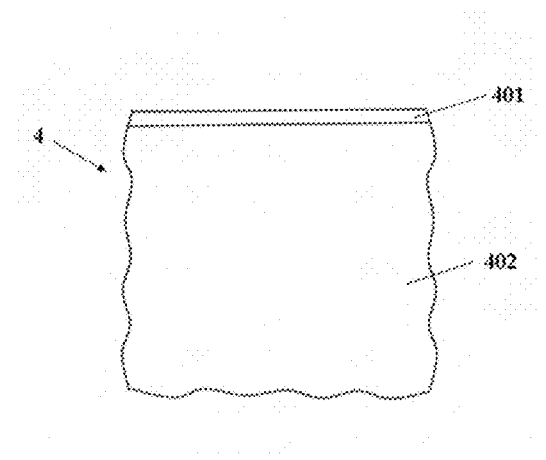
FIG. 6 is a schematic view showing a surface treatment layer of a moderator in an embodiment of the present disclosure.

Schematic diagram of the surface treatment layer of the moderator is referred to FIG. 6. The surface treatment layer 401 is coated on the surface of the substrate 402 of the moderator, wherein the surface treatment layer may be a single layer or a multi-layer structure, and the multi-layer structure may be a two-layer, three-layer, four-layer, five-layer structure; wherein the layers in the multi-layer structure may be the same material or different materials. The thickness of the surface treatment layer is not particularly limited, and different thicknesses may be selected depending on the material of the surface treatment layer and different processes, and the thickness is preferably 0.01 to 100 μm, and more preferably 0.1 to 10 μm. Preferably, the surface treatment layer is coated on the surface of the substrate by a method selected from the group consisting of covering, wrapping, pasting, electroplating, evaporation plating, electroless plating, spray plating, spray coating, dipping, vacuum evaporation, sputtering, deposition, or any combination thereof.

The moderator for moderating neutrons disclosed in the present disclosure is not limited to the contents described in the above embodiments and the structures shown in the drawings. Obvious modifications, substitutions, or alterations made to the materials, shapes and positions of the components in the present disclosure are within the scope of the present disclosure as claimed.

What is claimed is:

1. A moderator for moderating neutrons, comprising:
   a substrate prepared from a moderating material by a powder sintering device through a powder sintering process from powders or by compacting powders into a block, wherein the moderating material comprises 40% to 100% by weight of aluminum fluoride, and
   a surface treatment layer or a dry inert gas layer or a vacuum layer coated on the surface of the substrate, wherein the surface treatment layer is a hydrophobic material; and the surface treatment layer or the dry inert gas layer or the vacuum layer is provided for isolating the substrate from the water in ambient air.

2. The moderator according to claim 1, wherein the moderating material comprises 50 to 90% by weight of aluminum fluoride and optionally one or a mixture of two or more of lithium fluoride, aluminum, lead fluoride, aluminum oxide, calcium fluoride or magnesium fluoride.

3. The moderator according to claim 1, wherein the moderating material comprises 90 to 99.9% by weight of aluminum fluoride and optionally 0.1 to 10% by weight of lithium fluoride.

4. The moderator according to claim 1, wherein the moderator further comprises a first container, the dry inert gas layer is filled between the first container and the substrate, and the first container is provided for placing the substrate in an inert gas atmosphere.

5. The moderator according to claim 1, wherein the surface treatment layer is a removable surface treatment layer.

6. The moderator according to claim 1, wherein the moderator further comprises a second container, the vacuum layer is filled between the second container and the substrate, and the second container is provided for placing the substrate in a vacuum atmosphere.

7. The moderator according to claim 1, wherein the surface treatment layer is selected from the group consisting of a hydrophobic organic polymer, a hydrophobic inorganic polymer, or a combination thereof.

8. The moderator according to claim 7, wherein the hydrophobic organic polymer is selected from the group consisting of an organic fluoropolymer, a silicone polymer, a C2-20 substituted or unsubstituted olefinic polymer, a C2-20 substituted or unsubstituted alkynylic polymer, or a combination thereof.

9. The moderator according to claim 1, wherein the surface treatment layer is selected from the group consisting of an elemental metal, an alloy, a metal oxide, a metal fluoride, a metal nitride, a metal carbon oxynitride, silicon oxide, silicon nitride, or a combination thereof.

10. The moderator according to claim 9, wherein the metal fluoride is selected from the group consisting of magnesium fluoride, calcium fluoride, barium fluoride, lead fluoride, or a combination thereof.

11. The moderator according to claim 1, wherein the surface treatment layer is coated on the surface of the substrate by a method selected from the group consisting of covering, wrapping, pasting, electroplating, evaporation plating, electroless plating, spray plating, spray coating, dipping, vacuum evaporation, sputtering, deposition, or a combination thereof.

12. The moderator according to claim 1, wherein the surface treatment layer is a single layer or a multi-layer structure, and the multi-layer structure comprises two-layer, three-layer, four-layer and five-layer structure; and the layers in the multi-layer structure are the same material or different materials.

13. The moderator according to claim 1, wherein the surface treatment layer has a thickness of 0.01 to 100 μm.

14. The moderator according to claim 1, wherein the moderator is provided in a shape of two tapered sections that are adjacent to each other in opposite directions.

15. The moderator according to claim 14, wherein the moderator comprises a first diameter, a second diameter, and a third diameter, the length of the first diameter is 1 cm to 20 cm, the length of the second diameter is 30 cm to 100 cm, the length of the third diameter is 1 cm to 50 cm, and the material of the moderator has a density of 80% to 100% of the theoretical density.

16. A moderator for moderating neutrons, comprising:
   a substrate prepared from a moderating material by a powder sintering device through a powder sintering process from powders or by compacting powders into a block, wherein the moderating material comprises 40% to 100% by weight of aluminum fluoride, and
   a surface treatment layer or a dry inert gas layer or a vacuum layer coated on the surface of the substrate, wherein the surface treatment layer is a hydrophobic material; and the surface treatment layer or the dry inert gas layer or the vacuum layer is provided for isolating the substrate from the water in ambient air, wherein the moderator is provided for a beam shaping assembly, the beam shaping assembly including:
a beam inlet,
a target reacted with a proton beam from the beam inlet to produce neutrons,
a reflector adjacent to the target and surrounding the moderator, wherein the reflector leads deflected neutrons back to enhance epithermal neutron beam intensity,
a thermal neutron absorber adjacent to the moderator, wherein the thermal neutron absorber is used for absorbing thermal neutrons so as to avoid overdosing in superficial normal tissue during therapy,
a radiation shield disposed within the beam shaping assembly, wherein the radiation shield is provided for shielding leaking neutrons and photons so as to reduce dose of the normal tissue not exposed to irradiation, and
a beam exit.

17. The moderator for moderating neutrons according to claim 16, wherein the beam shaping assembly further comprises:
a third container, wherein the inert gas layer is filled between the third container and the substrate, and the third container is for placing the substrate of the moderator in the inert gas atmosphere; and/or
a fourth container, wherein the vacuum layer is located between the fourth container and the substrate, and the fourth container is for placing the substrate of the moderator in the vacuum atmosphere.

18. The moderator for moderating neutrons according to claim 16, wherein the beam shaping assembly further comprises a fifth container, wherein the fifth container is for placing the moderator, beam inlet, target, reflector, thermal neutron absorber, radiation shield, and beam exit of the shaping assembly in an inert gas atmosphere as described in the first aspect.

19. The moderator for moderating neutrons according to claim 16, wherein the beam shaping assembly is used for an accelerator boron neutron capture therapy, and the accelerator boron neutron capture therapy accelerates the proton beam by an accelerator, the target is made of metal, the proton beam is accelerated to an energy sufficient to overcome the coulomb repulsion of the target nucleus and undergo a nuclear reaction with the target to produce neutrons, the beam shaping assembly can moderate the neutrons to the epithermal neutron energy region and reduce the contents of thermal neutron and fast neutron, the epithermal energy region is between 0.5 eV and 40 keV, the thermal neutron energy region is less than 0.5 eV, and the fast neutron energy region is greater than 40 keV, the reflector is made of a material having a strong neutron reflection ability, and the thermal neutron absorber is made of a material having a large cross section with thermal neutrons.

20. A moderator for moderating neutrons, comprising:
a substrate prepared from a moderating material by a powder sintering device through a powder sintering process from powders or by compacting powders into a block, wherein the moderating material comprises 40% to 100% by weight of aluminum fluoride, and
a surface treatment layer or a dry inert gas layer or a vacuum layer coated on the surface of the substrate, wherein the surface treatment layer is a hydrophobic material; and the surface treatment layer or the dry inert gas layer or the vacuum layer is provided for isolating the substrate from the water in ambient air,
wherein the moderator is provided in a shape of two tapered sections that are adjacent to each other in opposite directions and for a beam shaping assembly, the beam shaping assembly including:
a beam inlet,
a target reacted with a proton beam from the beam inlet to produce neutrons,
a reflector adjacent to the target and surrounding the moderator, wherein the reflector leads deflected neutrons back to enhance epithermal neutron beam intensity,
a thermal neutron absorber adjacent to the moderator, wherein the thermal neutron absorber is used for absorbing thermal neutrons so as to avoid overdosing in superficial normal tissue during therapy,
a radiation shield disposed within the beam shaping assembly, wherein the radiation shield is provided for shielding leaking neutrons and photons so as to reduce dose of the normal tissue not exposed to irradiation, and
a beam exit.

* * * * *